(12) United States Patent
Subramanian et al.

(10) Patent No.: US 12,354,273 B2
(45) Date of Patent: Jul. 8, 2025

(54) MOVEMENT INDICATION

(71) Applicant: Nokia Technologies Oy, Espoo (FI)

(72) Inventors: Mahendran Subramanian, London (GB); Aldo Faisal, London (GB)

(73) Assignee: NOKIA TECHNOLOGIES OY, Espoo (FI)

( * ) Notice: Subject to any disclaimer, the term of this patent is extended or adjusted under 35 U.S.C. 154(b) by 505 days.

(21) Appl. No.: 17/413,371

(22) PCT Filed: Dec. 3, 2019

(86) PCT No.: PCT/EP2019/083387
§ 371 (c)(1),
(2) Date: Jun. 11, 2021

(87) PCT Pub. No.: WO2020/126452
PCT Pub. Date: Jun. 25, 2020

(65) Prior Publication Data
US 2022/0028082 A1  Jan. 27, 2022

(30) Foreign Application Priority Data

Dec. 19, 2018 (EP) .................... 18213990

(51) Int. Cl.
*G06T 7/00* (2017.01)
*A61B 5/00* (2006.01)
(Continued)

(52) U.S. Cl.
CPC .......... *G06T 7/0016* (2013.01); *A61B 5/0077* (2013.01); *A61B 5/0816* (2013.01);
(Continued)

(58) Field of Classification Search
CPC .......... G06T 7/0016; G06T 7/20; G06T 7/50; G06T 5/10; G06T 2207/10016;
(Continued)

(56) References Cited

U.S. PATENT DOCUMENTS 9,788,762 B2  10/2017  Auerbach
10,229,491 B1 *  3/2019  Rush .................. G06T 7/73
(Continued)

FOREIGN PATENT DOCUMENTS

CN   105869144 A    8/2016
EP     3245943 A1  11/2017
(Continued)

OTHER PUBLICATIONS

Vikram et al.,"A saliency model for goal directed actions" (published in 2012 IEEE International Conference on Development and Learning and Epigenetic Robotics (ICDL), Nov. 2012) (Year: 2012).*
(Continued)

*Primary Examiner* — Casey L Kretzer
(74) *Attorney, Agent, or Firm* — ALSTON & BIRD LLP

(57) ABSTRACT

An apparatus, method and computer program is described comprising: receiving depth data for a first plurality of pixels of a video image of a scene; determining depth data over time for each of a second plurality of pixels of the video image, wherein the second plurality of pixels comprises at least some of the first plurality of pixels; and processing the determined depth data of successive instances of the second plurality of pixels to generate movement data, wherein each instance of the second plurality of pixels comprises depth data of the second plurality of pixels.

20 Claims, 10 Drawing Sheets

(51) Int. Cl.

| | |
|---|---|
| *A61B 5/08* | (2006.01) |
| *A61B 5/11* | (2006.01) |
| *A61B 5/113* | (2006.01) |
| *G06T 5/10* | (2006.01) |
| *G06T 7/20* | (2017.01) |
| *G06T 7/50* | (2017.01) |
| *H04N 23/56* | (2023.01) |

(52) U.S. Cl.
CPC ............ *A61B 5/1128* (2013.01); *A61B 5/113* (2013.01); *G06T 5/10* (2013.01); *G06T 7/20* (2013.01); *G06T 7/50* (2017.01); *H04N 23/56* (2023.01); *G06T 2207/10016* (2013.01); *G06T 2207/10048* (2013.01); *G06T 2207/30004* (2013.01); *G06T 2207/30196* (2013.01)

(58) Field of Classification Search
CPC . G06T 2207/10048; G06T 2207/30004; G06T 2207/30196; A61B 5/0077; A61B 5/0816; A61B 5/1128; A61B 5/113; H04N 23/56
See application file for complete search history.

(56) References Cited

U.S. PATENT DOCUMENTS

| | | | | |
|---|---|---|---|---|
| 2003/0219147 | A1* | 11/2003 | Nishiura | G06T 7/20 382/103 |
| 2011/0172504 | A1* | 7/2011 | Wegerich | A61B 5/7264 600/301 |
| 2013/0116514 | A1* | 5/2013 | Kroner | A61B 5/316 600/509 |
| 2015/0073283 | A1* | 3/2015 | Van Vugt | A61B 5/4806 600/476 |
| 2015/0130841 | A1* | 5/2015 | Kohli | G16H 20/30 345/633 |
| 2016/0364617 | A1 | 12/2016 | Silberschatz et al. | |
| 2017/0055877 | A1 | 3/2017 | Niemeyer | |
| 2018/0053392 | A1 | 2/2018 | White et al. | |
| 2018/0064369 | A1 | 3/2018 | Gunther et al. | |
| 2020/0046302 | A1* | 2/2020 | Jacquel | A61B 5/0077 |

FOREIGN PATENT DOCUMENTS

| | | |
|---|---|---|
| KR | 1020160126238 A | 11/2016 |
| WO | 2020/126459 A1 | 6/2020 |

OTHER PUBLICATIONS https://www.amazon.com/Zoom-Kinect-Xbox-360/dp/B0050SYS5A.*
https://support.xbox.com/en-US/help/hardware-network/kinect/kinect-sensor-setup-tips.*
Office Action received for corresponding European Patent Application No. 18213990.7, dated Apr. 13, 2023, 6 pages.
Carney et al., "The Consensus Sleep Diary: Standardizing Prospective Sleep Self-Monitoring", Sleep, vol. 35, No. 2, Feb. 2012, pp. 287-302.
Grandner et al., "Sleep Disturbance is Associated with Cardiovascular and Metabolic Disorders", Journal of Sleep Research, vol. 21, No. 4, 2012, pp. 427-433.
"Dyssomnias", NCBI, Retrieved on Jun. 1, 2021, Webpage available at : https://www.ncbi.nlm.nih.gov/mesh/68020920.
Kelly et al., "Recent Developments in Home Sleep-Monitoring Devices", International Scholarly Research Network ISRN Neurology, vol. 2012, Article ID 768794, 2012, pp. 1-10.
Izadi et al., "KinectFusion: Real-time 3D Reconstruction and Interaction Using a Moving Depth Camera", In Proceedings of the 24th annual ACM symposium on User interface software and technology, Oct. 2011, 10 pages.
Henry et al., "RGB-D Mapping: Using Depth Cameras for Dense 3D Modeling of Indoor Environments", Experimental Robotics, 2014, pp. 1-15.
Maquet, "The Role of Sleep in Learning and Memory", Science, vol. 294, No. 5544, Nov. 2, 2001, pp. 1048-1052.
Colten et al., "Sleep Disorders and Sleep Deprivation: An Unmet Public Health Problem", National Academies Press (US), 2006, 424 pages.
Lavigne et al., "Restless Legs Syndrome and Sleep Bruxism: Prevalence and Association Among Canadians", Sleep, vol. 17, No. 8, 1994, pp. 739-743.
Punjabi, "The Epidemiology of Adult Obstructive Sleep Apnea", Proceedings of the American Thoracic Society, vol. 5, No. 2, 2008, pp. 136-143.
Patil et al., "Adult Obstructive Sleep Apnea: Pathophysiology and Diagnosis", Chest., vol. 132, No. 1, 2007, pp. 1-21.
Douglas et al., "Clinical Value of Polysomnography", The Lancet, vol. 339, Feb. 8, 1992, pp. 347-350.
Kushida et al., "Practice Parameters for the Indications for Polysomnography and Related Procedures: An Update for 2005", Sleep, vol. 28, No. 4, 2005, 23 pages.
De Souza et al., "Further Validation of Actigraphy for Sleep Studies", Sleep, 26, No. 1, 2003, pp. 81-85.
Ancoli-Israel et al., "The Role of Actigraphy in the Study of Sleep and Circadian Rhythms", Sleep, vol. 26, No. 3, 2003, pp. 342-392.
Sadeh et al., "The Role of Actigraphy in Sleep Medicine", Sleep Medicine Reviews, vol. 6, No. 2, May 2002, pp. 113-124.
Hoque et al., "Monitoring Body Positions and Movements During Sleep using WISPs", Proceeding WH '10 Wireless Health, Oct. 2010, pp. 44-53.
Liao et al., "Video-based Activity and Movement Pattern Analysis in Overnight Sleep Studies", 19th International Conference on Pattern Recognition (ICPR 2008), Dec. 8-11, 2008, 4 pages.
Scatena et al., "An Integrated Video-analysis Software System Designed for Movement Detection and Sleep Analysis. Validation of a Tool for the Behavioural Study of Sleep", Clinical Neurophysiology, vol. 123, No. 2, 2012, pp. 318-323.
Gavriel et al., "Towards Neurobehavioral Biomarkers for Longitudinal Monitoring of Neurodegeneration with Wearable Body Sensor Networks", 7th International IEEE/EMBS Conference on Neural Engineering (NER), Apr. 22-24, 2015, pp. 348-351.
Lee et al., "Monitoring and Analysis of Respiratory Patterns Using Microwave Doppler Radar", IEEE Journal of Translational Engineering in Health and Medicine, vol. 2, Oct. 2014, 12 pages.
Staderini, "UWB Radars in Medicine", IEEE Aerospace and Electronic Systems Magazine, vol. 17, No. 1, Jan. 2002, pp. 13-18.
Procházka et al., "Microsoft Kinect Visual and Depth Sensors for Breathing and Heart Rate Analysis", Sensors, vol. 16, Jun. 2016, pp. 1-11.
Al-Naji et al., "Real Time Apnoea Monitoring of Children Using the Microsoft Kinect Sensor: A Pilot Study", Sensors, vol. 17, No. 2, Feb. 2017, pp. 1-15.
Yu et al., "Breath and Position Monitoring during Sleeping with a Depth Camera", Proceeding of the International Conference on Health Informatics, 2012, pp. 12-22.
Khoshelham, "Accuracy Analysis of Kinect Depth Data", International Archives of the Photogrammetry, Remote Sensing and Spatial Information Sciences, 2011, pp. 133-138.
Smisek et al., "3D with Kinect", IEEE International Conference on Computer Vision Workshops (ICCV Workshops), Nov. 6-13, 2011, pp. 1154-1160.
Vifstad, "Sleep Movement Analysis using the Microsoft Kinect v1 Depth Sensor", Thesis, May 16, 2016, 95 pages.
"xef2mat", Github, Retrieved on Jun. 8, 2021, Webpage available at : https://github.com/raysworld/Xef2Mat.
Nguyen et al., "Modeling Kinect Sensor Noise for Improved 3D Reconstruction and Tracking", 2012 Second International Conference on 3D Imaging, Modeling, Processing, Visualization & Transmission, Oct. 13-15, 2012, pp. 524-530.
Mallick et al., "Characterizations of Noise in Kinect Depth Image: A Review", IEEE Sensors Journal, vol. 14, No. 6, Jun. 2014, pp. 1731-1740.

(56) References Cited

OTHER PUBLICATIONS

Essmaeel et al., "Comparative Evaluation of Methods for Filtering Kinect Depth Data", Multimedia Tools and Applications, vol. 74, No. 17, 2015, pp. 7331-7354.
Camplani et al., "Adaptive Spatio-Temporal Filter for Low-Cost Camera Depth Maps", IEEE International Conference on Emerging Signal Processing Applications, Jan. 12-14, 2012, pp. 33-36.
Wasenmuller et al., "Comparison of Kinect V1 and V2 Depth Images in Terms of Accuracy and Precision", Asian Conference on Computer Vision Workshop (ACCV workshop), Nov. 2016, pp. 1-12.
Xia et al., "A Real-time Respiratory Motion Monitoring System using KINECT: Proof of Concept", Medical Physics, vol. 39, No. 5, May 2012, pp. 2682-2685.
Nijholt, "Contactless Respiration Monitoring using a 30 Camera System", Thesis, Dec. 2016, 82 pages.
Martinez et al., "Breathing Rate Monitoring During Sleep From a Depth Camera Under Real-life Conditions", IEEE Winter Conference on Applications of Computer Vision (WACV), Mar. 24-31, 2017, 9 pages.
Benetazzo et al., "Respiratory Rate Detection Algorithm Based on RGB-D Camera: Theoretical Background and Experimental Results", Healthcare Technology Letters, vol. 1, No. 3, Sep. 2014, 13 pages.
Lee et al., "Sleep Monitoring System Using Kinect Sensor", International Journal of Distributed Sensor Networks, vol. 2015, Article ID 875371, 2015, 10 pages.
Gill et al., "A System for Change Detection and Human Recognition in Voxel Space using the Microsoft Kinect Sensor", IEEE Applied Imagery Pattern Recognition Workshop (AIPR), Oct. 11-13, 2011, 8 pages.
Rother et al., "Grabcut: Interactive Foreground Extraction using Iterated Graph Cuts", ACM Transactions on Graphics, vol. 23, No. 3, Aug. 2004, pp. 309-314.
Madadi et al., "Multi-part Body Segmentation based on Depth Maps for Soft Biometry Analysis", Pattern Recognition Letters, vol. 56, Feb. 2015, pp. 1-7.
Palmero et al., "Automatic Sleep System Recommendation by Multi-modal RBG-Depth-Pressure Anthropometric Analysis", International Journal of Computer Vision, vol. 122, No. 2, Apr. 2017, 16 pages.
Bylow wt al., "Real-Time Camera Tracking and 3D Reconstruction Using Signed Distance Functions", Robotics: Science and Systems, Jun. 2013, 8 pages.
Min et al., "Depth Video Enhancement Based on Weighted Mode Filtering", IEEE Transactions on Image Processing, vol. 21, No. 3, Mar. 2012, pp. 1176-1190.
Suarez et al., "Hand Gesture Recognition with Depth Images: A Review", IEEE RO-MAN: The 21st IEEE International Symposium on Robot and Human Interactive Communication, Sep. 9-13, 2012, pp. 411-417.
Yu et al., "Multiparameter Sleep Monitoring Using a Depth Camera", Communications in Computer and Information Science, vol. 357, 2012, 15 pages.
Extended European Search Report received for corresponding European Patent Application No. 18213990.7, dated Apr. 12, 2019, 9 pages.
"Random Sample Consensus", Wikipedia, Retrieved on Jun. 8, 2021, Webpage available at : https://en.wikipedia.org/wiki/Random_sample_consensus.
Kempfle et al., "Respiration Rate Estimation with Depth Cameras: An Evaluation of Parameters", Proceedings of the 5th international Workshop on Sensor-based Activity Recognition and Interaction, Sep. 2018, 10 pages.
Office Action received for corresponding European Patent Application No. 18213990.7, dated Jun. 21, 2021, 5 pages.
Bakhtiyari et al., "KinRes: Depth Sensor Noise Reduction in Contactless Respiratory Monitoring", Proceedings of the 11th EAI International Conference on Pervasive Computing Technologies for Healthcare, May 2017, 4 pages.
International Search Report and Written Opinion received for corresponding Patent Cooperation Treaty Application No. PCT/EP2019/083387, dated Jan. 21, 2020, 14 pages.
Office Action received for corresponding European Patent Application No. 18213990.7, dated Feb. 22, 2021, 5 pages.
Gyaourova et al., "Block Matching for Object Tracking", US Department of Energy, UCRL-TR-200271, Oct. 14, 2003, 15 pages.
Office Action received for corresponding European Patent Application No. 18213990.7, dated Sep. 21, 2022, 4 pages.
Intention to Grant for European Application No. 18213990.7 dated Mar. 6, 2025, 8 pages.

\* cited by examiner

MOVEMENT INDICATION

RELATED APPLICATION

This application claims priority to PCT Application No. PCT/EP2019/083387, filed on 3 Dec. 2019, which claims priority to European Application No. 18213990.7, filed on 19 Dec. 2018, each of which is incorporated herein by reference in its entirety.

FIELD

This specification relates to generating a movement indication for a scene.

BACKGROUND

Motion data can be extracted from video data. Information, such as breathing data for a human subject, can be extracted from said motion data. However, there remains a need for alternative arrangements for generating and using motion data.

SUMMARY

In a first aspect there is described an apparatus comprising: means for receiving depth data for a first plurality of pixels of a video image of a scene; means for determining depth data over time for each of a second plurality of pixels of the video image, wherein the second plurality of pixels comprises at least some of the first plurality of pixels; and means for processing the determined depth data of successive instances of the second plurality of pixels to generate movement data, wherein each instance of the second plurality of pixels comprises depth data of the second plurality of pixels.

The movement data may comprise breathing pattern data, and/or pulse data.

The second plurality of pixels may be non-contiguous.

The second plurality of pixels may comprise a random or pseudo-random selection of the pixels of the video image.

The apparatus may further comprise means for selecting said second plurality of pixels such that a distribution of said second plurality of pixels complies with a distribution function.

The apparatus may further comprise means for sensing said depth data.

The means for sensing said depth data may comprise a multi-modal camera including an infrared projector and an infrared sensor.

The means for processing the depth data may perform frequency domain filtering.

The frequency domain filtering may identify movements with frequencies in a normal range of breathing rates.

The apparatus may further comprise means for determining a mean distance measurement for the second plurality of pixels between their two successive instances.

The means for processing the determined depth data may generate said movement data based, at least in part, on determining whether a mean distance measurement between successive instances of depth data is greater than a threshold value.

The second plurality of pixels may be a subset of the first plurality of pixels, or the first plurality of pixels and the second plurality of pixels may be identical.

The various means of the apparatus may comprise: at least one processor; and at least one memory including computer program code, the at least one memory and the computer program code configured, with the at least one processor, to cause the performance of the method of the second aspect, below.

In a second aspect, there is provided a method comprising: receiving depth data for a first plurality of pixels of a video image of a scene; determining depth data over time for each of a second plurality of pixels of the video image, wherein the second plurality of pixels comprises at least some of the first plurality of pixels; and processing the determined depth data of successive instances of the second plurality of pixels to generate movement data, wherein each instance of the second plurality of pixels comprises depth data of the second plurality of pixels.

The movement data may comprise breathing pattern data, and/or pulse data.

The second plurality of pixels may be non-contiguous.

The second plurality of pixels may comprise a random or pseudo-random selection of the pixels of the video image.

The method may further comprise selecting said second plurality of pixels such that a distribution of said second plurality of pixels complies with a distribution function.

The method may further comprise sensing said depth data.

Sensing said depth data may comprise using a multi-modal camera including an infrared projector and an infrared sensor.

Processing the depth data may comprise frequency domain filtering.

The frequency domain filtering may identify movements with frequencies in a normal range of breathing rates.

The method may further comprise determining a mean distance measurement for the second plurality of pixels between their two successive instances.

Processing the determined depth data may generate said movement data based, at least in part, on determining whether a mean distance measurement between successive instances of depth data is greater than a threshold value.

The second plurality of pixels may be a subset of the first plurality of pixels, or the first plurality of pixels and the second plurality of pixels may be identical.

In a third aspect, this specification describes any apparatus configured to perform any method as described with reference to the second aspect.

In a fourth aspect, this specification describes computer-readable instructions which, when executed by computing apparatus, cause the computing apparatus to perform any method as described with reference to the second aspect.

In a fifth aspect, this specification describes a computer program comprising instructions for causing an apparatus to perform at least the following: receive video data for a scene; determine a movement measurement for at least some of a plurality of subframes of the video data; weight the movement measurements to generate a plurality of weighted movement measurements, wherein the weighting is dependent on the subframe; and generate a movement indication for the scene from a combination (such as a sum) of some or all of the weighted movement measurements.

In a sixth aspect, this specification describes a computer-readable medium (such as a non-transitory computer readable medium) comprising program instructions stored thereon for performing at least the following: receive depth data for a first plurality of pixels of a video image of a scene; determine depth data over time for each of a second plurality of pixels of the video image, wherein the second plurality of pixels comprises at least some of the first plurality of pixels; and process the determined depth data of successive instances of the second plurality of pixels to generate movement data, wherein each instance of the second plurality of pixels comprises depth data of the second plurality of pixels.

In a seventh aspect, this specification describes an apparatus comprising: at least one processor; and at least one memory including computer program code which, when executed by the at least one processor, causes the apparatus to: receive depth data for a first plurality of pixels of a video image of a scene; determine depth data over time for each of a second plurality of pixels of the video image, wherein the second plurality of pixels comprises at least some of the first plurality of pixels; and process the determined depth data of successive instances of the second plurality of pixels to generate movement data, wherein each instance of the second plurality of pixels comprises depth data of the second plurality of pixels.

In an eighth aspect, this specification describes an apparatus comprising: a first input for receiving depth data for a first plurality of pixels of a video image of a scene; a first control module for determining depth data over time for each of a second plurality of pixels of the video image, wherein the second plurality of pixels comprises at least some of the first plurality of pixels; and a second control module for processing the determined depth data of successive instances of the second plurality of pixels to generate movement data, wherein each instance of the second plurality of pixels comprises depth data of the second plurality of pixels. The first and second control modules may be combined.

BRIEF DESCRIPTION OF THE DRAWINGS

Examples will now be described, by way of non-limiting examples, with reference to the following schematic drawings, in which.

DETAILED DESCRIPTION

Sleep disorders are associated with many problems, including psychiatric and medical problems. Sleep disorders are sometimes divided into a number of subcategories, such as intrinsic sleep disorders, extrinsic sleep disorders and circadian rhythm based sleep disorders.

Examples of intrinsic sleep disorders include idiopathic hypersomnia, narcolepsy, periodic limb movement disorder, restless legs syndrome, sleep apnoea and sleep state misperception.

Examples of extrinsic sleep disorders include alcohol-dependent sleep disorder, food allergy insomnia and inadequate sleep routine.

Examples of circadian rhythm sleep disorders include advanced sleep phase syndrome, delayed sleep phase syndrome, jetlag and shift worker sleep disorder.

Better understanding of sleep physiology and pathophysiology may aid in improving the care received by individuals suffering with such difficulties. Many sleep disorders are primarily diagnosed based on self-reported complaints. Lack of objective data can hinder case understanding and care provided. By way of example, data relating to breathing patterns of a patient may be valuable.

Non-contact, discrete longitudinal home monitoring may represent the most suitable option for monitoring sleep quality (including breathing patterns) over a period of time and may, for example, be preferred to clinic-based monitoring as the sleep patterns can vary between days depending on food intake, lifestyle and health status.

Figure 1:
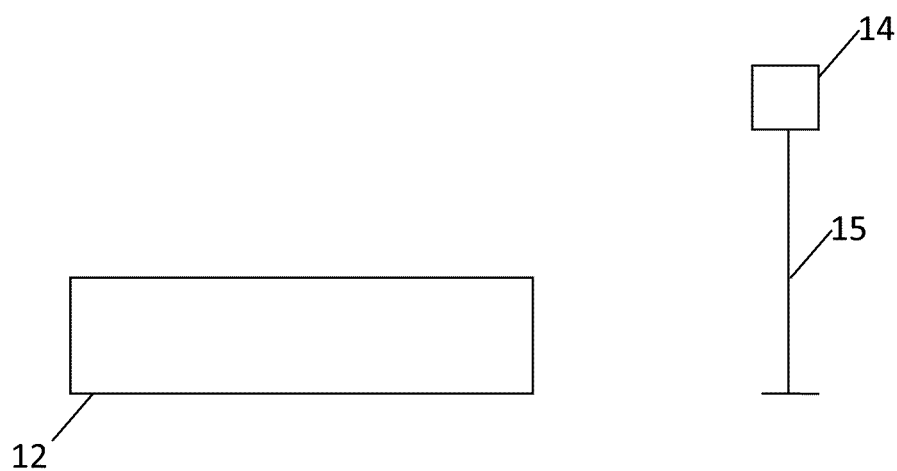
FIG. 1 is block diagram of a system in accordance with an example embodiment.

FIG. 1 is block diagram of a system, indicated generally by the reference numeral 10, in accordance with an example embodiment. The system 10 includes a bed 12 and a depth camera 14. The depth camera may, for example, be mounted on a tripod 15. As discussed further below, the depth camera 14 may capture both depth data and video data of a scene including the bed 12 (and any patient on the bed).

In the use of the system 10, a patient may sleep on the bed 12, with the depth camera 14 being used to record aspects of sleep quality (such as breathing patterns indicated by patient movement). The bed 12 may, for example, be in a patient's home, thereby enabling home monitoring, potentially over an extended period of time.

Figure 2:
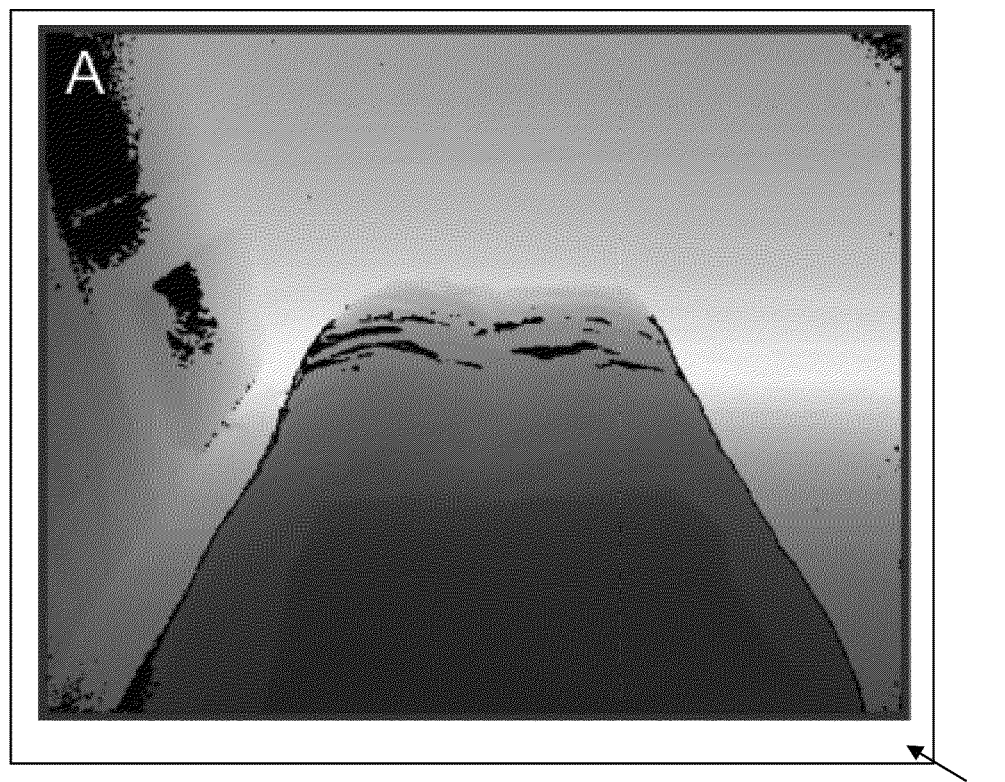
FIG. 2 shows an example image in accordance with an example embodiment.

FIG. 2 shows an example output, indicated generally by the reference numeral 20, in accordance with an example embodiment. The output 20 is an example of depth data generated by the depth camera 14 of the system 10. The depth data may be data of a scene that is fixed. For example, the scene may be captured using a camera having a fixed position and having unchanging direction and zoom. In this way, changes in the depth data can be monitored over time (e.g. over several hours of sleep) and may be compared with other data (e.g. collected over days, weeks or longer and/or collected from other users).

The depth camera 14 may produce depth matrices, where each element of the matrix corresponds to the distance from an object in the image to the depth camera. The depth matrices can be converted to grey images, as shown in FIG. 2 (e.g. the darker the pixel, the closer it is to the sensor). If the object is too close or too far away, the pixels may be set to zero such that they appear black.

Figure 3:
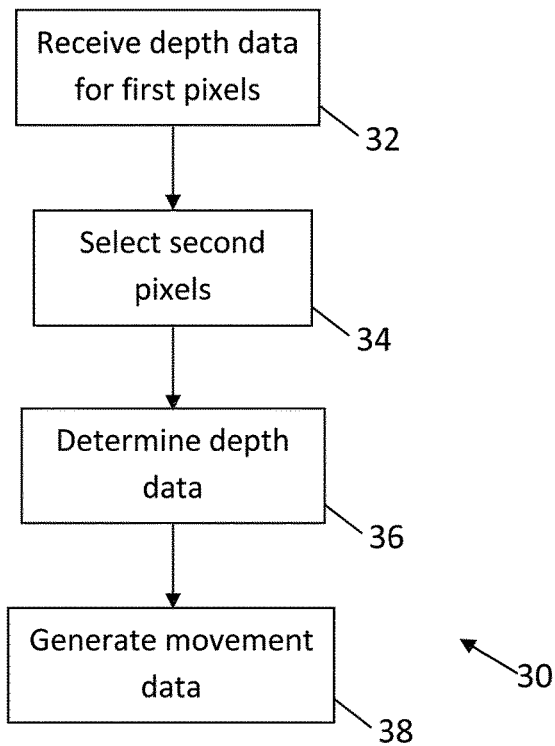
FIG. 3 is a flow chart showing an algorithm in accordance with an example embodiment.

FIG. 3 is a flow chart showing an algorithm, indicated generally by the reference numeral 30, in accordance with an example embodiment.

The algorithm 30 starts at operation 32, where depth data is received (for example from the camera 14 described above). The depth camera 14 (e.g. a camera incorporating an RGB-D sensor) may determine depth data for a first plurality of pixels of an image of a scene. The scene may relate to a human subject, for example captured during sleep.

Where the term "image" is used herein, it is to be understood that the image may be a video image, for example a series of frames of image data.

An example depth camera may capture per-pixel depth information via infra-red (IR) mediated structured light patterns with stereo sensing or time-of-flight sensing to generate a depth map. Some depth cameras include three-dimensional sensing capabilities allowing synchronized image streaming of depth information. Many other sensors are possible.

Figure 4:
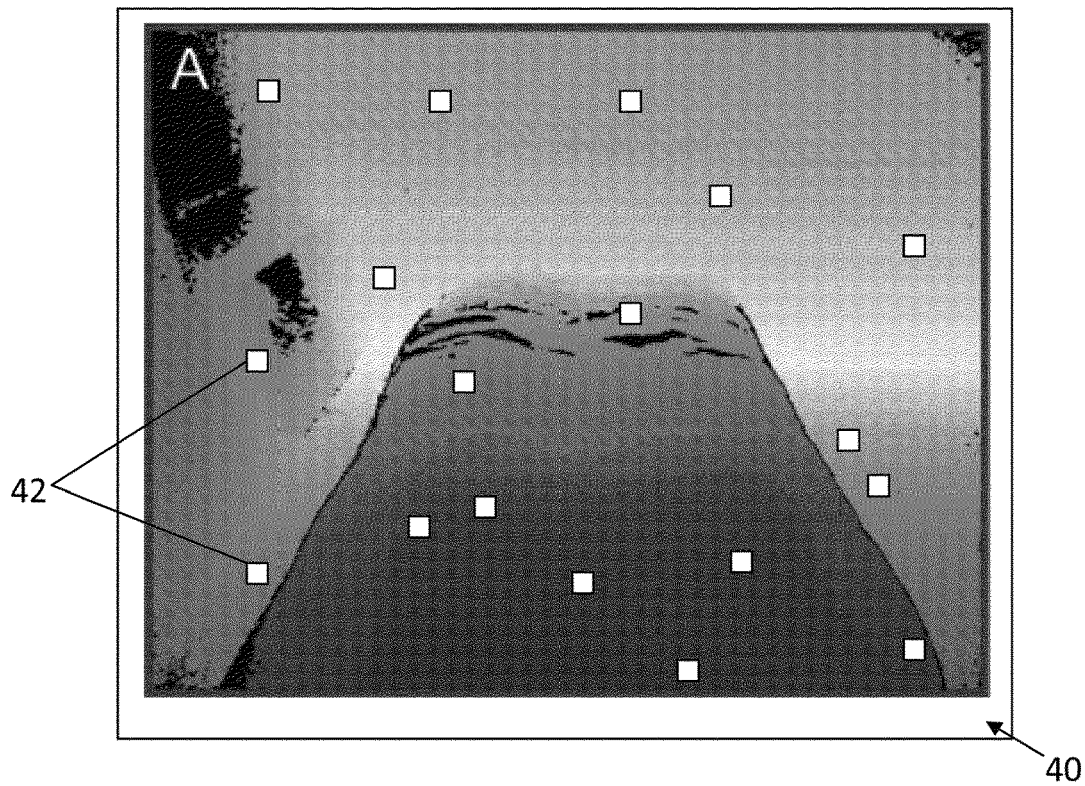
FIG. 4 shows an example image being processed in accordance with an example embodiment.

At operation 34, a second plurality of pixels is selected. By way of example, FIG. 4 shows an example output, indicated generally by the reference numeral 40, in accordance with an example embodiment. The output 40 shows the data of the output 20 and also shows the second plurality of pixels 42 (two of which are labelled in FIG. 4). The second plurality of pixels may be randomly (or pseudo-randomly) selected from the plurality of pixels of the image 20 (although, as discussed further below, other distributions of the pixels 42 are possible). (Note that the pixels 42 are shown as relatively large pixels to ensure that they are visible in FIG. 4. In reality, such pixels may be smaller.)

As shown in FIG. 4, the second plurality of pixels may be non-contiguous, for example distributed across the extent of the image of the scene. In this way, the second plurality of pixels can provide a plurality of "pinpricks" of data from the overall image. Clearly, the use of a plurality of pinprick-pixels can significantly reduce data storage and processing requirements when compared with considering the entire image. By "non-contiguous" it is meant that the second plurality of pixels are not located in such a way that they form a single contiguous area. In practice, the non-contiguous pixels may be located in a plurality of smaller contiguous groups that are not contiguous with one another. However, the best coverage of the scene may be obtained by ensuring the such groups are as small as possible, for example that each group is less than a threshold number of pixels. In some examples, the threshold number of pixels may be 2, such that none of the second plurality of pixels is located immediately adjacent another.

The first plurality of pixels (obtain in the operation 32) may include data from all pixels in the image 40; however, this is not essential in all examples. Thus, the first plurality of pixels may be a subset of the full set of pixels of the image.

The second plurality of pixels comprises some or all of the first plurality of pixels. (In the event that the second plurality of pixels comprises all of the first plurality of pixels, the operation 34 may be omitted.) Thus, whilst is some embodiments the second plurality of pixels is a subset of the first plurality of pixels, in other embodiments, the first and second plurality of pixels may be identical.

At operation 36, depth data for successive instances of the second plurality of pixels are determined to generate data that can be used to provide an indication of a degree of movement between one instance of depth data and the next.

Finally, a movement indication, based on the outputs of the operation 36, is provided in operation 38. By way of example, the operation 38 may determine whether movement is detected in any of the second plurality of pixels. Alternatively, the movement indication may be generated from a combination (such as a sum, e.g. a weighted sum) of some or all of the second plurality of pixels.

The movement data generated in operation 38 is based on the depth data determined in operation 36. Each instance of the second plurality of pixels comprises depth data of a consistent set of pixels of the scene such that the movement data is derived from data from the same set of pixels collected over time. In one example implementation, the successive instances of the of the second plurality of pixels were separated by 5 seconds (although, of course, other separations are possible). Separating successive instances of the depth data by a period such as 5 seconds even if more data are available may increase the likelihood of measurable movement occurring between instances and may reduce the data storage and processing requirements of the system.

More generally, an instance of one or more pixel may be the values of those pixels at a particular moment in time, for example in a single frame of a in a stream of image data such as a video. Successive instances of the pixel(s) may be adjacent frames of the stream. Alternatively, the video stream may be sampled at instances of time with successive instances of pixels being the values of pixels at each sample. Described above is an example where the sample period is used that is a fixed temporal value (e.g. a certain number of seconds); however, other approaches to sampling may be used. For example, the stream may be sampled (and an instance of the pixel(s) defined) in response to a repeating event that does not have a fixed period—for example each time a detected noise level associated with the monitored scene increases above a threshold amount, in which case the change in pixel data will be representative of movement between successive noises. Many possible approaches can be used to determine when an instance of the pixel data is defined As discussed further below, the movement measurements for each of the second plurality of pixels of the depth data may be determined on the basis of the mean distance evolution of the pixels. A distance measurement may be determined for the second plurality of pixels of each measurement instance, with the distance measurement enabling one measurement instance to be compared with other measurement instance(s).

The movement data generated in the operation 38 provides movement data for the second plurality of pixels. However, as discussed further below, movement in the second plurality of pixels may be representative of movement in the overall image. Moreover, by using only a subset of data points in the image (perhaps for a subset of time instance in the obtained data), the quantity of data stored and/or processed can be substantially reduced.

Figure 5:
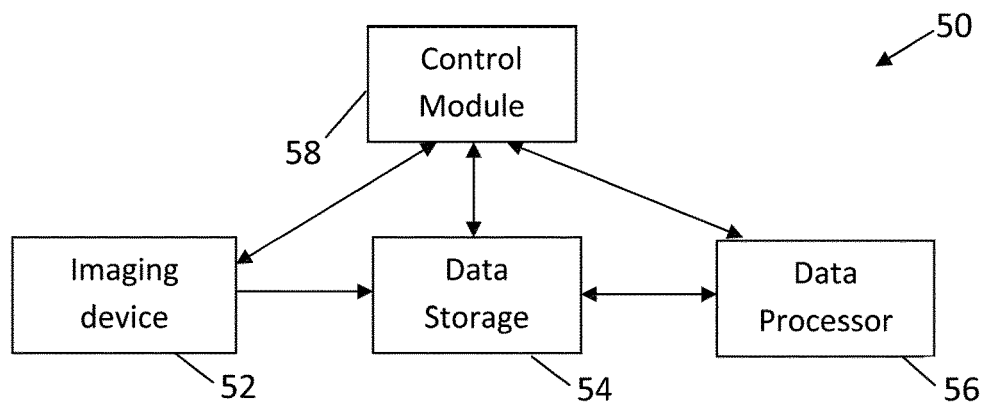
FIG. 5 is block diagram of a system in accordance with an example embodiment.

FIG. 5 is block diagram of a system, indicated generally by the reference numeral 50, in accordance with an example embodiment. The system 50 comprises an imaging device 52 (such as the camera 14), a data storage module 54, a data processing module 56 and a control module 58.

The data storage module 54 may store measurement data (e.g. the depth data for the first plurality of pixels, as obtained in the operation 32 of the algorithm 30) under the control of the control module 58, with the stored data being processed by data processor 56 to generate an output (e.g. the output of the operation 38 of the operation 30). The output may be provided to the control module 58. In an alternative arrangement, the data storage module 54 may store the depth data of the second plurality of depth data (e.g.

outputs of the operation 34), with the stored data being processed by data processor 56 to generate the output (e.g. the output of the operation 38). A potential advantage of storing the second plurality of data is a reduced data storage requirement.

The camera 14 of the system 10 and/or the imaging device 52 of the system 50 may be a multimodal camera comprising a colour (RGB) camera and an infrared (IR) projector and infrared sensor. The sensor may send an array of near infra-red (IR) light into the field-of-view of the camera 14 or the imaging device 52, with a detector receiving reflected IR and an image sensor (e.g. a CMOS image sensor) running computational algorithms to construct a real-time, three-dimensional depth value mesh-based video. Information obtained and processed in this way may be used, for example, to identify individuals, their movements, gestures and body properties and/or may be used to measure size, volume and/or to classify objects. Images from depth cameras can also be used for obstacle detection by locating a floor and walls.

In one example implementation, the imaging device 52 was implemented using a Kinect® camera provided by the Microsoft Corporation. In one example, the frame rate of the imaging device 52 was 33 frames per second.

Depth frames may be captured by the imaging device 52 and stored in the data storage module 54 (e.g. in the form of binary files). In an example implementation, the data storage 54 was used to record depth frames for subjects sleeping for period ranging between 5 and 8 hours. In one example implementation, the data storage requirement for one night of sleep was of the order of 200 GB when the entirety of each frame was stored; however, it was possible to reduce this storage requirement by approximately 98% using the approach described herein.

The stored data can be processed by the data processor 56. The data processing may be online (e.g. during data collection), offline (e.g. after data collection) or a combination of the two. The data processor 56 may provide an output, as discussed further below.

Figure 6:
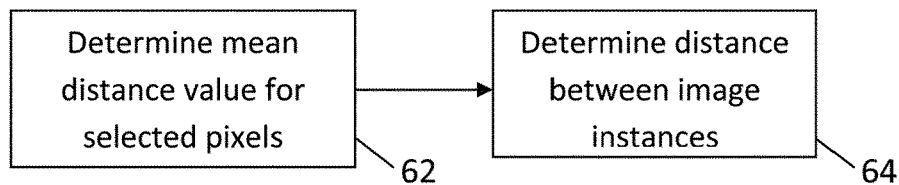
FIG. 6 is a flow chart showing an algorithm in accordance with an example embodiment.

FIG. 6 is a flow chart showing an algorithm, indicated generally by the reference numeral 60, showing an example implementation of the operation 38 of the algorithm 30, in accordance with an example embodiment. As described above, the operation 38 determines movement between successive instances of the captured depth data.

The algorithm 60 starts at operation 62 where a mean distance value for the second plurality of pixels of an image is determined. Then, at operation 64, distances between images instances (based on the distances determined in operation 62) are determined. As discussed further below, a distance between images instances that is higher than a threshold value may be indicative of movement between successive images.

By way of example, consider the depth data of the second plurality of pixels generated in the operation 36.

After removing all the zero pixels in the frames the mean distance of the second plurality of pixels at instance i is defined by:

$$M(i) = \frac{1}{N} \times \sum_{k=1}^{N} D(k, i) \quad (1)$$

Where:
D∈G\Z with
G={set of pixels in the second plurality}; and
Z={set of zero value pixels in the second plurality}.

In this context, the "distance" of a pixel refers to the difference in its depth between the two instances. For example, if the pixel has a depth of 150 cm in a first instance and a depth of 151 cm in a second instance then the distance of the pixel between the two instances is 151−150=1 cm.

Having computed the mean distance of the second plurality of pixels of successive frames of a dataset (the operation 62), a determination of distance between image instances (indicative of movement in the relevant scene) can be made (the operation 64).

One method for determining movement is as follows. First, a mean is defined based on the set of all the non-zero value pixels. Next, if the difference between the mean distance of two consecutive frames is above a certain threshold $\theta_1$, a change in position is noticed. This is given by: $M(i)-M(i-1) \geq \theta_1$.

Several values based on standard deviations and maximum differences are tested in order to find the best threshold values (as discussed further below).

Figure 7:
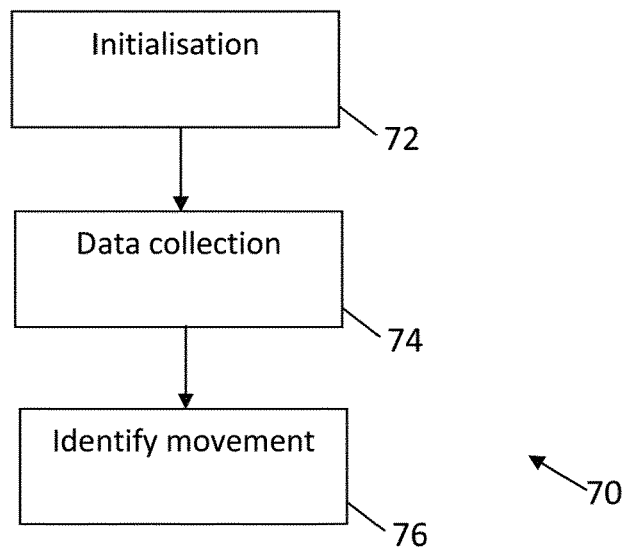
FIG. 7 is a flow chart showing an algorithm in accordance with an example embodiment.

FIG. 7 is a flow chart showing an algorithm, indicated generally by the reference numeral 70, in accordance with an example embodiment. The algorithm 70 starts at operation 72 where an initialisation phase is carried out. The initialisation phase is conducted without a patient being present (such that there should be no movement detected). As described below, the initialisation phase is used to determine a noise level in the data. Next, at operation 74, a data collection phase is carried out. Finally, at operation 76, instances of the data collected in operation 74 having data indicative of movement are identified (thereby implementing the operation 38 of the algorithm 30 described above). The instances identified in operation 76 are based on a threshold distance level that is set depending on the noise level determined in the operation 72.

Figure 8:
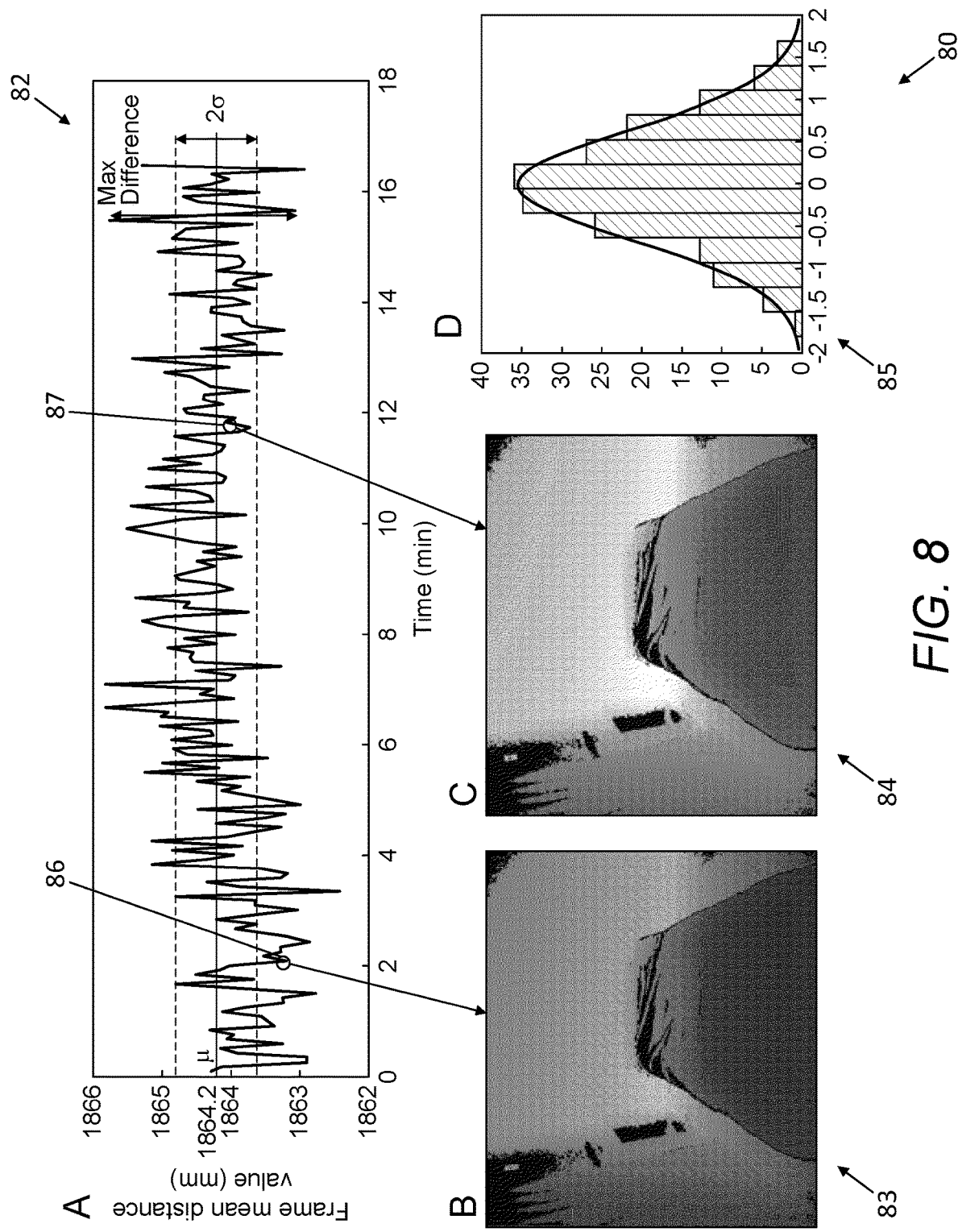
FIG. 8 shows an initialisation data in accordance with an example embodiment.

FIG. 8 shows an initialisation data, indicated generally by the reference numeral 80 in accordance with an example embodiment. The initialisation data 80 includes mean distance data 82, a first image 83, a second image 84 and a representation of the noise 85. The first image 83 corresponds to the mean distance data of a data point 86 and the second image 84 corresponds to the mean distance data of a data point 87.

It should be noted that although the data 80 may be based on full images (similar to the image 20 discussed above), similar initialisation data could have been generated based on the second plurality of pixels described above.

The mean distance data 82 shows how the determined mean frame distance changes over time (a time period of 18 minutes is shown in FIG. 8). As the data 80 was collected without motion (e.g. without a patient being on the bed 12 of the system 10), the variations in the mean distance data 82 are representative of noise. The noise representation 85 expresses the noise as a Gaussian distribution. That distribution can be used to determine a standard deviation for the noise data (as indicated by the standard deviation shown in the data 82). A maximum difference between two consecutive mean values is also plotted on the output 80.

The operation 72 seeks to assess the intrinsic noise in the frames of the output 80. In this way, the intrinsic variation in the data at rest can be determined so that the detection of motion will not be confused by noise.

The operation 72 may be implemented using the principles of the algorithm 30 described above. Thus, video data (i.e. the output 82) may be received. Distances in the selected second plurality of pixels can then be determined (see operation 36 of the algorithm 30). (Although, as noted above, the noise could be based on the entire image, e.g. the first plurality of pixels.)

In the data collection phase 74 of the algorithm 70, the subject goes to sleep and the relevant dataset is collected. Then, in operation 76, the knowledge of the noise is exploited to determine the likelihood that a change in distance data is indicative of actual movement (rather than noise). By way of example, movement may be deemed to have occurred in the event that determined distance data is more than 55 standard deviations (as determined in operation 72) away from the previous mean distance.

An experiment has been conducted on fourteen nights including eleven different subjects in order to validate the reproducibility of the experiment. The data were stored as videos which serve as ground truth. The true detection of movements was manually noted looking at the videos and was compared to the detection of movements provided by the algorithm being tested.

Figure 9A:
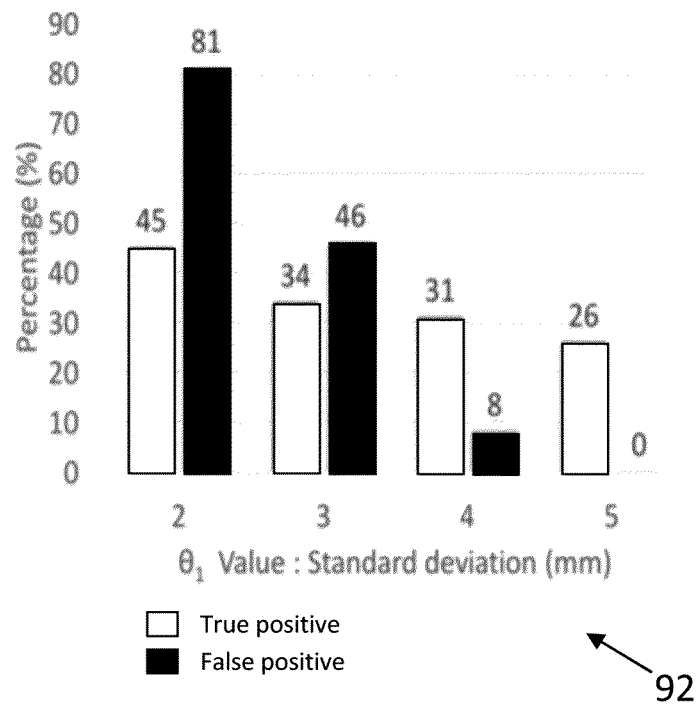
FIGS. 9A and 9B show results in accordance with an example embodiment.
Figure 9B:
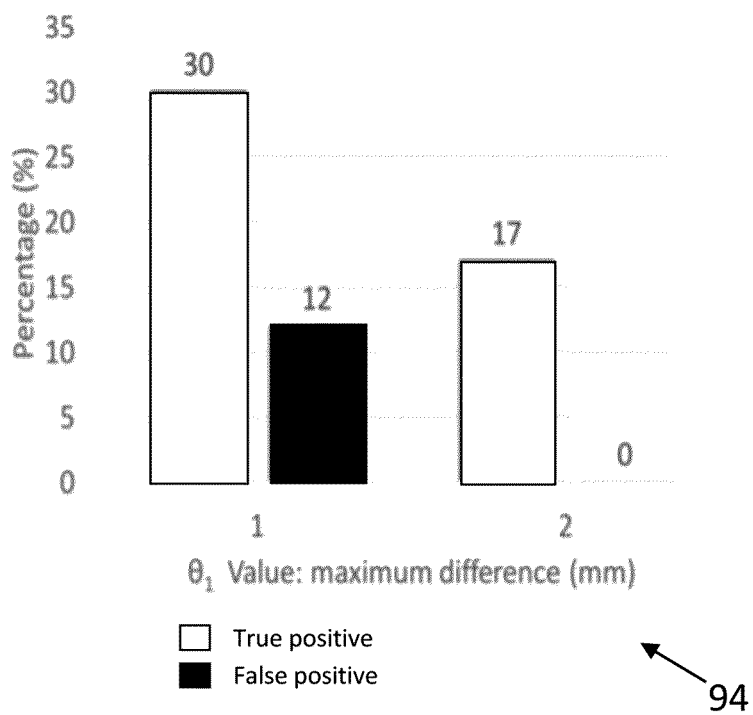

FIGS. 9A and 9B show results, indicated generally by the reference numerals 92 and 94 respectively, in accordance with example embodiments. The results are based on a mean distance evolution (i.e. how the mean distance determinations change over time) for the fourteen subjects. The percent of good detection (true positives) averaging all experiments is shown together with the overestimation of movements (false positives). The results 92 and 94 are based on frames of image data having the form described above with reference to FIG. 2 (i.e. without selecting a subset of the pixels for processing).

The results 92 show the number of correct movement identifications (true positives) and the number of false movement identification (false positives) for different standard deviation threshold levels. With the movement threshold at two standard deviations (such that a mean distance change of at least two standard deviations is detected), a true positives measurement of 45% was detected and a false positives measurements of 81% was detected. As the threshold level was increased, the number of false positives reduced (to zero at five standard deviations). However, at five standard deviations, the true positives level had reduced to 26%. Accordingly, the results 92 show poor performance.

The results 94 show the number of correct movement identifications (true positives) and the number of false movement identification (false positives) when using maximum distance differences as the threshold value. The performance was also poor.

Figure 10A:
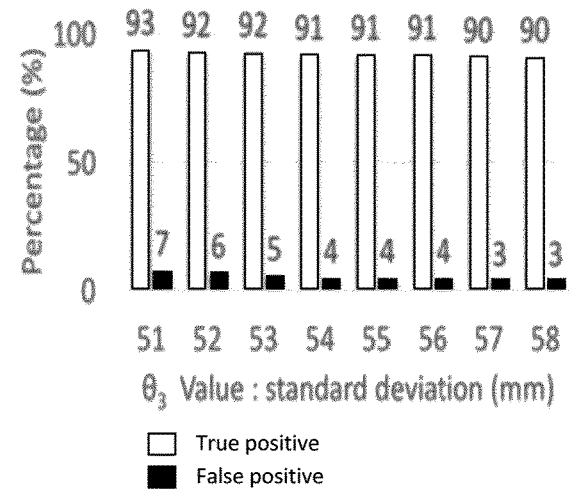
FIGS. 10A and 10B show results in accordance with an example embodiment.
Figure 10B:
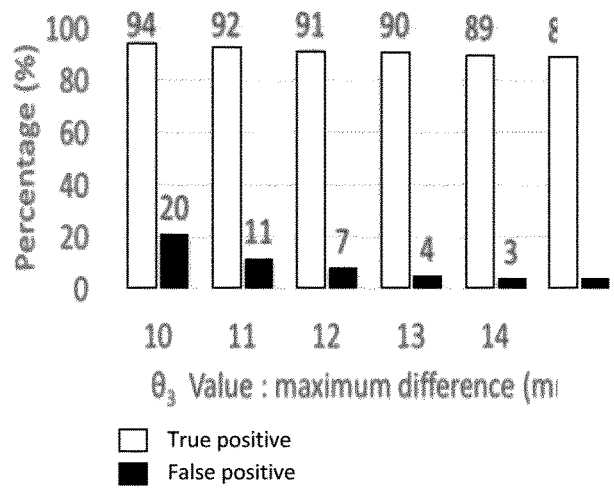

FIGS. 10A and 10B show results, indicated generally by the reference numerals 102 and 104 respectively, in accordance with example embodiments. The results are based on a mean distance evolution for the fourteen subjects. The percent of good detection (true positives) averaging all experiments is shown together with the overestimation of movements (false positives). The results 102 and 104 are based on considering pixel depth evolution of a plurality of pixels of image data (e.g. the second plurality of pixels discussed above).

The results 102 show the number of correct movement identifications (true positives) and the number of false movement identification (false positives) for different standard deviation threshold levels. With the movement threshold at 55 standard deviations, a true positives measurement of 91% was detected and a false positives measurement of 4% was detected. Thus, the results for the second plurality of pixels were significantly better than the results for the full frame arrangement described above with reference to FIGS. 9A and 9B. The results 104 show a similarly good performance when using maximum distance differences as the threshold value.

Figure 11:
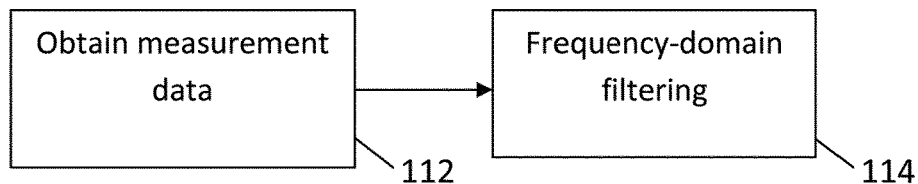
FIG. 11 is a flow chart showing an algorithm in accordance with an example embodiment.

FIG. 11 is a flow chart showing an algorithm, indicated generally by the reference numeral 110, in accordance with an example embodiment.

The algorithm 110 starts at operation 112 where measurement data is obtained by sensing. The operation 112 may, for example, implement some or all of the algorithms 30 or 70 described above. The operation 112 may, for example, provide data indicative of movement over time.

At operation 114, frequency-domain filtering of the measurement data is conducted. Thus, the operation 114 may implement means for processing determined changes in depth data by incorporating frequency domain filtering. Such filtering may, for example, be used to identify movement with frequencies within a particular range.

One example use of the principles described herein is in the monitoring of breathing patterns of a patient. In such an embodiment, the operation 114 may perform frequency-domain filtering in order to identify movements with frequencies in a normal range of breathing rates. Thus, movement data can be filtered to identify movement that might be indicative of breathing. For example, a band-pass filter centred on typical breathing frequencies may be used to implement the operation 114.

Figure 12:
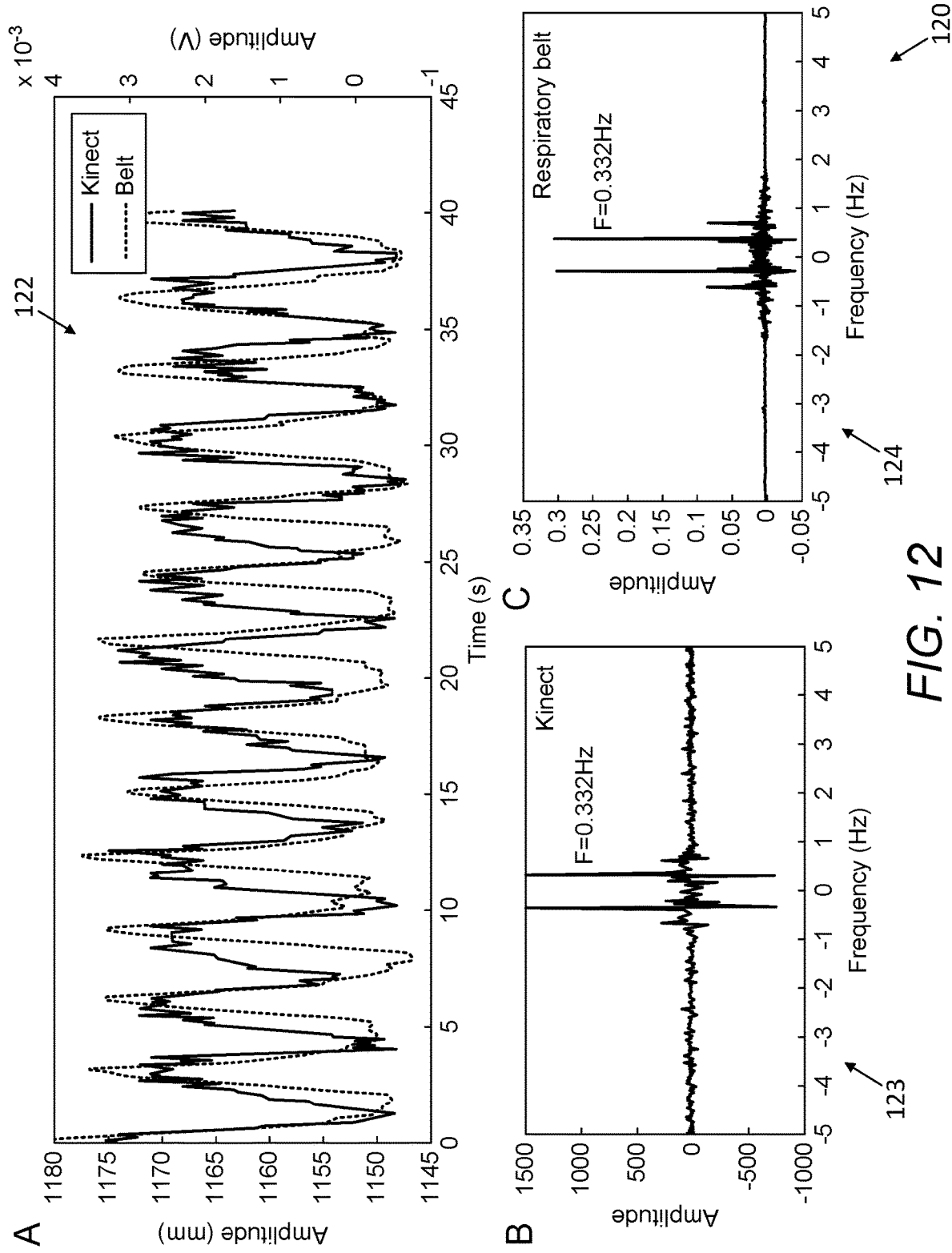
FIG. 12 shows output data in accordance with an example embodiment.

FIG. 12 shows output data, indicated generally by the reference numeral 120, in accordance with an example embodiment. The data 120 compares the performance of depth data processing in accordance with the principles described herein (labelled "Kinect" in FIG. 12), with the performance of a measurement belt (labelled "Belt" in FIG. 12).

The output 122 shows the "Kinect" and "Belt" performance in the time domain, wherein movement amplitude is plotted against time. The output 123 shows the "Kinect" performance in the frequency domain. The output 124 shows the "Belt" performance in the frequency domain.

As can be seen in FIG. 12, the performance of depth data processing in accordance with an example embodiment described herein ("Kinect") is similar to the performance of with an example measurement belt ("Belt").

In the arrangement described above with reference to FIG. 4, the selection of pixels (in operation 34 of the algorithm 30) was random (or pseudorandom). In other embodiments, the selection of pixels may be subject to a distribution function (with or without a random or pseudorandom element). A variety of functions are described herein (which functions may be used alone or in any combination).

Figure 13:
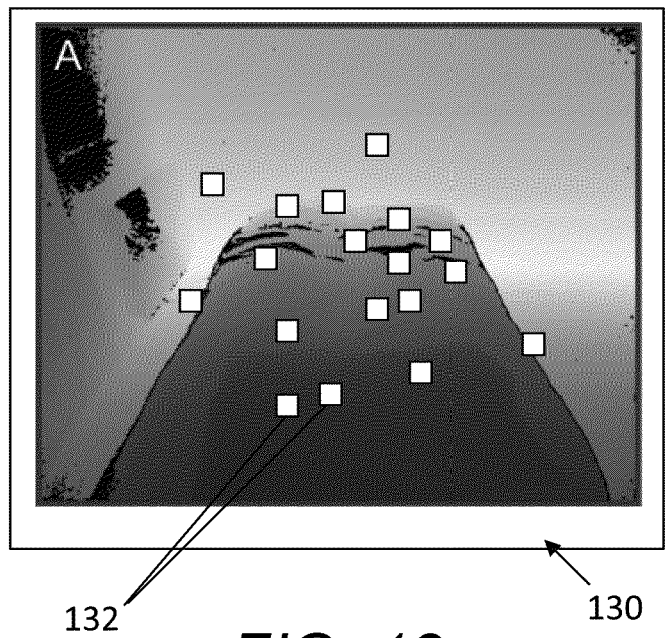
FIG. 13 shows an example image being processed in accordance with an example embodiment.

FIG. 13 shows an example image, indicated generally by the reference numeral 130, being processed in accordance with an example embodiment. A plurality of pixels 132 that collectively form the pixels selected in the operation 34 are shown. The pixels are spread according to a function that favours locations close to the centre of the image. The distribution 130 also has a random element. The logic here is that the camera/imaging device is likely to be directed such that objects of interest are close to the centre of the field of view.

The weighting of a distribution function may be at least partially dependent on visual characteristics of the scene. For example, areas above the level of the bed 12 in the system 10 described above may be weighted higher in a distribution function than areas with surfaces below the surface on the bed (on the assumption that movement is more likely to occur above the level of the bed than below the level of the bed). Alternatively, or in addition, areas on the bed 12 in the system 10 may be weighted higher in the distribution function. The second plurality of pixels may be selected on the basis of such distribution functions, favouring pixel locations within areas that have a higher weighting.

Figure 14:
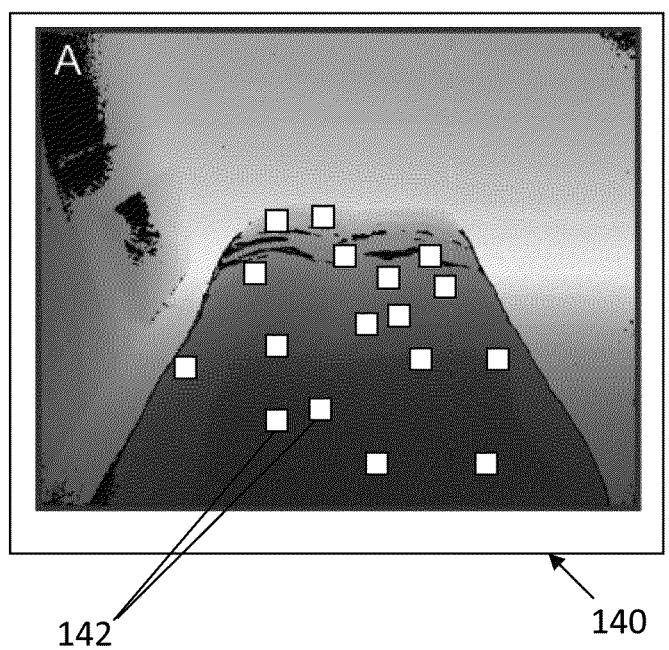
FIG. 14 shows an example image being processed in accordance with an example embodiment.

FIG. 14 shows an example image, indicated generally by the reference numeral 140, being processed in accordance with an example embodiment. A plurality of pixels 142 that collectively form the pixels selected in the operation 34 are shown. The pixels are spread randomly (or pseudo-randomly) but subject to being positioned on a bed identified in the image. The logic here is that a sleeping patient can be expected to be located on the bed.

The examples described above generally relate to sleep monitoring in general, and the detection of data relating to sleep disorders in particular. This is not essential to all embodiments. For example, the principles discussed herein can be used to determine movement in a scene for other purposes. For example, a similar approach may be taken to detect movement in a largely static scene, for example for monitoring an area to detect the movement of people, animals, vehicles, etc. within it.

Moreover, the examples described above generally relate to determining breathing patterns of a patient. This is not essential to all embodiments. Many other movements may be detected. For example, the principles described herein could be applied to the detection of a heartbeat of a patient.

Figure 15:
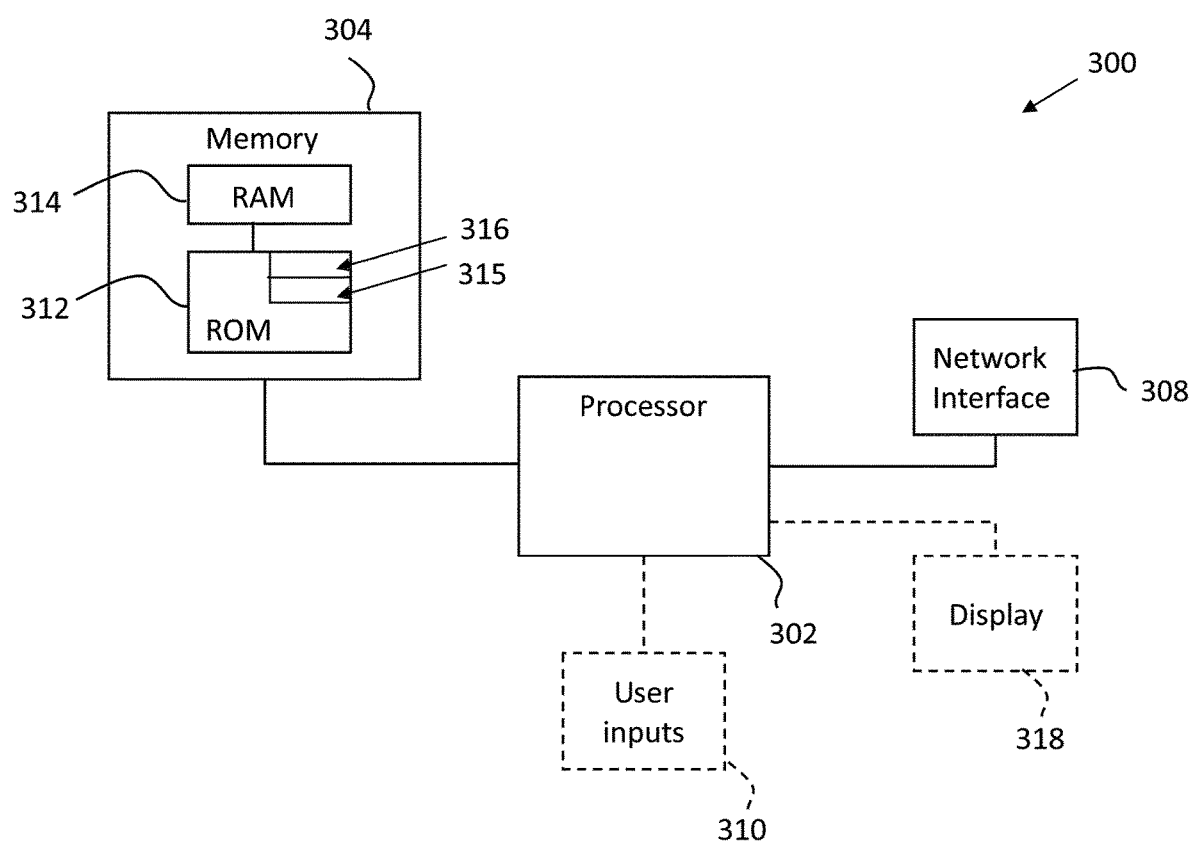
FIG. 15 is a block diagram of a system in accordance with an example embodiment.

For completeness, FIG. 15 is a schematic diagram of components of one or more of the example embodiments described previously, which hereafter are referred to generically as processing systems 300. A processing system 300 may have a processor 302, a memory 304 closely coupled to the processor and comprised of a RAM 314 and ROM 312, and, optionally, user input 310 and a display 318. The processing system 300 may comprise one or more network/apparatus interfaces 308 for connection to a network/apparatus, e.g. a modem which may be wired or wireless. Interface 308 may also operate as a connection to other apparatus such as device/apparatus which is not network side apparatus. Thus direct connection between devices/apparatus without network participation is possible. User input 310 and display 318 may be connected to a remote processor like ground control station. Remote connection may be LTE or 5G type fast connection between remote processor and processor.

The processor 302 is connected to each of the other components in order to control operation thereof.

The memory 304 may comprise a non-volatile memory, such as a hard disk drive (HDD) or a solid state drive (SSD). The ROM 312 of the memory 314 stores, amongst other things, an operating system 315 and may store software applications 316. The RAM 314 of the memory 304 is used by the processor 302 for the temporary storage of data. The operating system 315 may contain code which, when executed by the processor implements aspects of the algorithms 30, 60, 70 and 110 described above. Note that in the case of small device/apparatus the memory can be most suitable for small size usage i.e. not always hard disk drive (HDD) or solid state drive (SSD) is used.

The processor 302 may take any suitable form. For instance, it may be a microcontroller, a plurality of microcontrollers, a processor, or a plurality of processors.

The processing system 300 may be a standalone computer, a server, a console, or a network thereof. The processing system 300 and needed structural parts may be all inside device/apparatus such as IoT device/apparatus i.e. embedded to very small size.

In some example embodiments, the processing system 300 may also be associated with external software applications. These may be applications stored on a remote server device/apparatus and may run partly or exclusively on the remote server device/apparatus. These applications may be termed cloud-hosted applications. The processing system 300 may be in communication with the remote server device/apparatus in order to utilize the software application stored there.

Figure 16A:
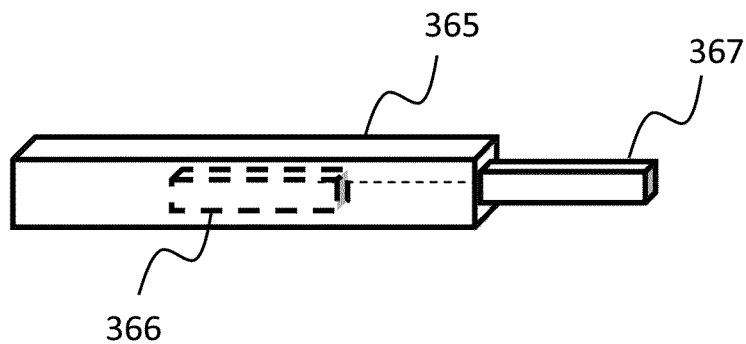
FIGS. 16A and 16B show tangible media, respectively a removable memory unit and a compact disc (CD) storing computer-readable code which when run by a computer perform operations according to example embodiments.
Figure 16B:
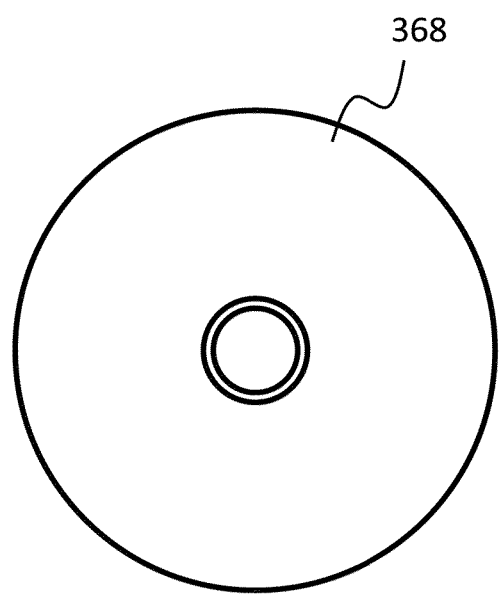

FIGS. 16A and 16B show tangible media, respectively a removable memory unit 365 and a compact disc (CD) 368, storing computer-readable code which when run by a computer may perform methods according to example embodiments described above. The removable memory unit 365 may be a memory stick, e.g. a USB memory stick, having internal memory 366 storing the computer-readable code. The memory 366 may be accessed by a computer system via a connector 367. The CD 368 may be a CD-ROM or a DVD or similar. Other forms of tangible storage media may be used. Tangible media can be any device/apparatus capable of storing data/information which data/information can be exchanged between devices/apparatus/network.

Embodiments of the present invention may be implemented in software, hardware, application logic or a combination of software, hardware and application logic. The software, application logic and/or hardware may reside on memory, or any computer media. In an example embodiment, the application logic, software or an instruction set is maintained on any one of various conventional computer-readable media. In the context of this document, a "memory" or "computer-readable medium" may be any non-transitory media or means that can contain, store, communicate, propagate or transport the instructions for use by or in connection with an instruction execution system, apparatus, or device, such as a computer.

Reference to, where relevant, "computer-readable storage medium", "computer program product", "tangibly embodied computer program" etc., or a "processor" or "processing circuitry" etc. should be understood to encompass not only computers having differing architectures such as single/multi-processor architectures and sequencers/parallel architectures, but also specialised circuits such as field programmable gate arrays FPGA, application specify circuits ASIC, signal processing devices/apparatus and other devices/apparatus. References to computer program, instructions, code etc. should be understood to express software for a programmable processor firmware such as the programmable content of a hardware device/apparatus as instructions for a processor or configured or configuration settings for a fixed function device/apparatus, gate array, programmable logic device/apparatus, etc.

As used in this application, the term "circuitry" refers to all of the following: (a) hardware-only circuit implementations (such as implementations in only analogue and/or digital circuitry) and (b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a server, to perform various functions) and (c) to circuits, such as a microprocessor(s) or a portion of a microprocessor(s), that require software or firmware for operation, even if the software or firmware is not physically present.

If desired, the different functions discussed herein may be performed in a different order and/or concurrently with each other. Furthermore, if desired, one or more of the above-described functions may be optional or may be combined. Similarly, it will also be appreciated that the flow diagrams of FIGS. 3, 6, 7 and 11 are examples only and that various operations depicted therein may be omitted, reordered and/or combined.

It will be appreciated that the above described example embodiments are purely illustrative and are not limiting on the scope of the invention. Other variations and modifications will be apparent to persons skilled in the art upon reading the present specification. For example, it would be possible to extend the principles described herein to other applications, such as the control of robots or similar objects.

Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

Although various aspects of the invention are set out in the independent claims, other aspects of the invention comprise other combinations of features from the described example embodiments and/or the dependent claims with the features of the independent claims, and not solely the combinations explicitly set out in the claims.

It is also noted herein that while the above describes various examples, these descriptions should not be viewed in a limiting sense. Rather, there are several variations and modifications which may be made without departing from the scope of the present invention as defined in the appended claims.

The invention claimed is:

1. An apparatus comprising:
at least one processor; and
at least one memory including computer program code;
the at least one memory and the computer program code configured to, with the at least one processor, cause the apparatus at least to perform:
receiving depth data for a first plurality of pixels of a video image of a monitored scene, wherein the depth data is captured using a camera comprising a fixed position with unchanging direction and zoom;
determining depth data over time for each of a second plurality of pixels of the video image, wherein the second plurality of pixels comprises at least some of the first plurality of pixels, and wherein the second plurality of pixels are non-contiguous and are not located to form a single contiguous area; and
processing the determined depth data of successive instances of the second plurality of pixels to generate movement data, wherein respective instances of the second plurality of pixels comprises depth data of the second plurality of pixels, and wherein processing the determined depth data comprises selecting the successive instances based on sampling a video stream of the monitored scene in response to a detected noise level satisfying a threshold amount.

2. An apparatus as claimed in claim 1, wherein said movement data comprises breathing pattern data.

3. An apparatus as claimed in claim 1, wherein said second plurality of pixels comprises a random or pseudo-random selection of the pixels of the video image identified to be within a region of the monitored scene comprising a bed.

4. An apparatus as claimed in claim 1, wherein the at least one memory and the computer program code configured to, with the at least one processor, further cause the apparatus at least to perform: selecting said second plurality of pixels such that a distribution of said second plurality of pixels complies with a distribution function.

5. An apparatus as claimed in claim 1, wherein the at least one memory and the computer program code configured to, with the at least one processor, further cause the apparatus at least to perform: sensing said depth data.

6. An apparatus as claimed in claim 5, wherein a multi-modal camera including an infrared projector and an infrared sensor is used for sensing said depth data.

7. An apparatus as claimed in claim 1, wherein processing the depth data comprises performing frequency domain filtering that identifies movements with frequencies in a normal range of breathing rates.

8. An apparatus as claimed in claim 1, wherein the at least one memory and the computer program code configured to, with the at least one processor, further cause the apparatus at least to perform: determining a mean distance measurement for the second plurality of pixels between their two successive instances.

9. An apparatus as claimed in claim 8, wherein processing the determined depth data generates said movement data based, at least in part, on determining whether a mean distance measurement between successive instances of depth data is greater than a threshold value.

10. An apparatus as claimed in claim 1, wherein:
the second plurality of pixels is a subset of the first plurality of pixels; or
the first plurality of pixels and the second plurality of pixels are identical.

11. An apparatus as claimed in claim 1, wherein said movement data is used to determine a quality of sleep of a user.

12. An apparatus as claimed in claim 1, wherein the depth data comprises one or more depth matrices, and wherein one or more elements of respective ones of the one or more depth matrices corresponds to a distance from an object in the image to the camera.

13. An apparatus as claimed in claim 1, wherein the second plurality of pixels are located in a plurality of smaller contiguous groups that are not contiguous with one another, and wherein respective ones of the plurality of smaller contiguous groups comprise less pixels than a threshold number of pixels.

14. A method comprising:
receiving depth data for a first plurality of pixels of a video image of a monitored scene, wherein the depth data is captured using a camera comprising a fixed position with unchanging direction and zoom;
determining depth data over time for each of a second plurality of pixels of the video image, wherein the second plurality of pixels comprises at least some of the first plurality of pixels, and wherein the second plurality of pixels are non-contiguous and are not located to form a single contiguous area; and
processing the determined depth data of successive instances of the second plurality of pixels to generate movement data, wherein each instance of the second plurality of pixels comprises depth data of the second plurality of pixels, and wherein processing the determined depth data comprises selecting the successive instances based on sampling a video stream of the monitored scene in response to a detected noise level satisfying a threshold amount.

15. A method as claimed in claim 14, wherein said movement data comprises breathing pattern data.

16. A method as claimed in claim 14, wherein said second plurality of pixels comprises a random or pseudo-random selection of the pixels of the video image identified to be within a region of the monitored scene comprising a bed.

17. A method as claimed in claim 14, further comprising selecting said second plurality of pixels such that a distribution of said second plurality of pixels complies with a distribution function.

18. A method as claimed in claim 14, further comprising sensing said depth data.

19. A method as claimed in claim 14, wherein processing the depth data comprises performing frequency domain filtering.

20. A non-transitory computer-readable medium comprising program instructions for causing an apparatus to perform at least the following:

receiving depth data for a first plurality of pixels of a video image of a monitored scene, wherein the depth data is captured using a camera comprising a fixed position with unchanging direction and zoom;

determining depth data over time for each of a second plurality of pixels of the video image, wherein the second plurality of pixels comprises at least some of the first plurality of pixels, and wherein the second plurality of pixels are non-contiguous and are not located to form a single contiguous area; and processing the determined depth data of successive instances of the second plurality of pixels to generate movement data, wherein each instance of the second plurality of pixels comprises depth data of the second plurality of pixels, and wherein processing the determined depth data comprises selecting the successive instances based on sampling a video stream of the monitored scene in response to a detected noise level satisfying a threshold amount.

* * * * *